United States Patent [19]
Hoganson

[11] 3,984,081
[45] Oct. 5, 1976

[54] MEDICAL DEVICE FOR CONTROLLING FLOW OF INTRAVENOUS SOLUTIONS

[75] Inventor: Carolyn Lee Hoganson, Halifax, Canada

[73] Assignee: The Raymond Lee Organization, Inc., a part interest

[22] Filed: Oct. 25, 1974

[21] Appl. No.: 517,903

[52] U.S. Cl. .................. 251/6; 24/115 L; 24/136 A
[51] Int. Cl.² ................................ F16K 7/06
[58] Field of Search .................. 251/4, 6, 7, 9; 24/136 A, 171, 244, 194, 115 L, 155 BR, 263 SW; 403/368, 374

[56] References Cited
UNITED STATES PATENTS

| | | | |
|---|---|---|---|
| 1,259,584 | 3/1918 | Anderson | 24/263 SW X |
| 2,245,030 | 6/1941 | Gottesfeld | 24/136 A |
| 2,412,097 | 12/1946 | Russell | 251/6 X |
| 2,595,511 | 5/1952 | Butler | 251/6 |
| 2,643,848 | 6/1953 | Hoffmann | 251/7 X |
| 2,804,092 | 8/1957 | Aitchison | 251/9 X |
| 3,497,175 | 2/1970 | Koland | 251/9 |

Primary Examiner—Martin P. Schwadron
Assistant Examiner—Richard Gerard

[57] ABSTRACT

A vertically elongated hollow rectangular box with vertical walls and an open top and bottom has a downwardly and rearwardly extending slot in one side wall. The forward edge of the slot bears a series of arcuate rearwardly facing notches cut into the housing. A removable bar rides in the slot, and bears a knob exterior the housing. When a flexible tube or hose is placed along the rear wall in the interior of the housing, the bar gradually contricts its diameter as the bar is moved downwardly in the slot. The notches keep the bar in place.

1 Claim, 4 Drawing Figures

MEDICAL DEVICE FOR CONTROLLING FLOW OF INTRAVENOUS SOLUTIONS

SUMMARY OF THE INVENTION

In medical applications, it is often necessary to regulate the rate of flow of fluids administered intravenously within very precisely specified limits. Customarily this is done by an individual using measuring instruments and the like who monitors the operation continuously. This invention is directed toward a device which can be used to regulate the rate of flow and continuous monitoring by an operator is not needed.

In this invention, a vertical hollow housing is adapted to receive a flexible tube or hose through which the fluid to be administered flows. The housing also receives a bar. The hose is disposed inside the housing and extends along a rear wall thereof. A side wall of the housing has an oblique downwardly and rearwardly extending slot through which the bar passes. The bar can be moved manually in the slot. As the bar is moved downward therein, it pinches the tube ever more tightly against the rear wall. This pinching action constricts the diameter of the tube and reduces the rate of flow of fluid therethrough as compared to the unrestricted rate of flow. Means keep the bar in position so that it is not pressed upwardly in the slot by the pressure of the hose against it. Consequently, the rate of flow of fluid is controlled as desired.

DETAILED DESCRIPTION OF PREFERRED EMBODIMENTS

Figure 1:
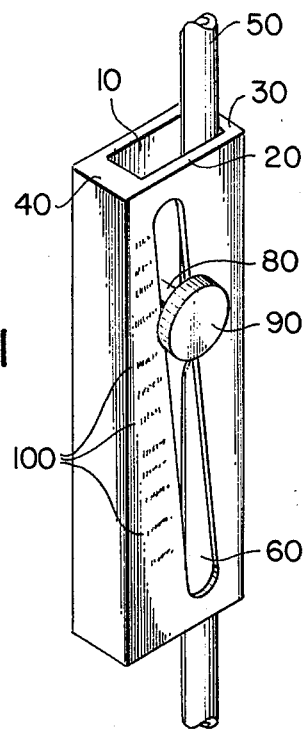
FIG. 1 is a drawing of the invention in use.
Figure 2:
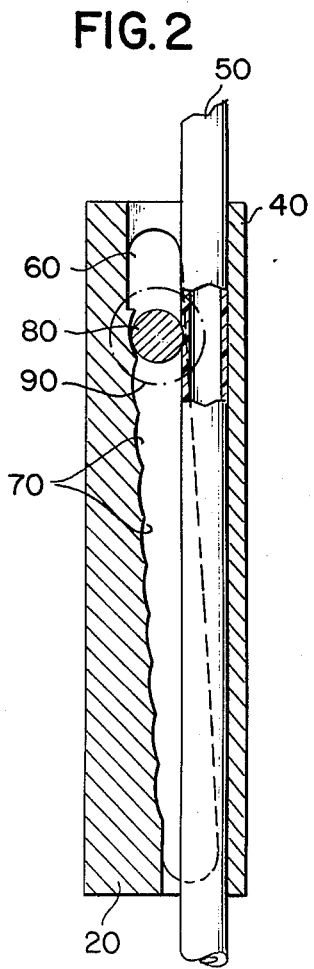
FIG. 2 is a cross section showing the invention set to provide minimal hose constriction.
Figure 3:
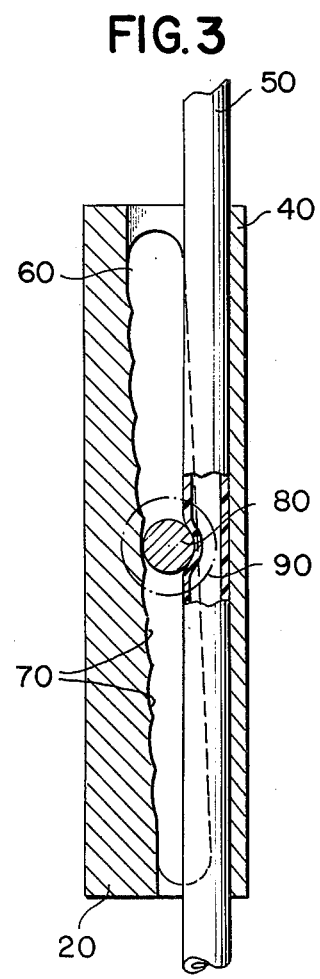
FIG. 3 is a view similar to FIG. 2 but providing moderate hose constriction.
Figure 4:
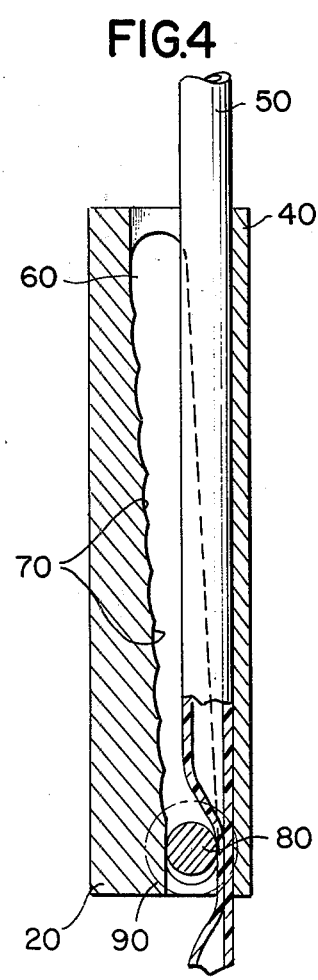
FIG. 4 is a view similar to FIG. 3 but providing maximum hose constriction.

A housing is formed from two side walls 10 and 20, a rear wall 30 and a front wall 40, the walls all being vertical and forming a hollow vertically elongated rectangular box with an open top and bottom. A flexible hose or length of tubing 50 is disposed inside the housing along the rear wall. Side wall 20 bears a downwardly and rearwardly extending slot 60, the front edge of the slot having a series of like arcuate, rearwardly facing notches 70.

Inside the slot, wedged between the forward edge of the slot and the hose, and extending transversely through the slot, is a removable horizontal bar 80, that increasingly constricts the diameter of the hose as it is moved downwardly in the slot. A cylindrical knob 90 is attached to the end of the bar exterior the housing. The knob provides an easy handle for grasping and moving the bar along the slot to various valving positions or withdrawing the bar from the slot to immediately restore full flow.

If desired, fluid flow calibrations 100 may be marked on wall 20 adjacent the notches, for calibrating the rate of fluid flow through the hose at various degrees of constriction.

In order to prevent the bar from slipping out of a selected position, each notch can have a central recess in which the bar can be disposed. The recess serves as a lock, since the bar must be manually removed therefrom and cannot be accidentally displaced because of pressure of the hose or the like.

While the invention has been described with particular reference to the drawings, the protection sought should be limited only by the terms of the claim which follows.

What is claimed is:

1. A device for constricting the diameter of a flexible hose comprising:

a vertically elongated hollow housing with the shape of a rectangular box and with four vertical walls open at its top and bottom ends, the housing having a slot in one and only one of its side walls, the slot being inclined longitudinally with respect to the rear wall and having a plurality of congruent arcuate rearwardly facing notches cut into the forward edge of the slot;

calibrations denoting rates of fluid flow inscribed on the outside of the housing next to the notches in the slot;

a horizontal, rigid bar removably located in the slot for increasingly constricting the diameter of a flexible fluid-carrying hose that has been passed through the housing along the rear wall as the bar is located lower down in the slot by squeezing the hose between the rear wall and the bar; and a control knob attached to the bar outside the housing for grasping by an operator to move the bar along the slot to various valving positions or to withdraw the bar from the slot to immediately restore full flow.

* * * * *